United States Patent [19]

Forsythe, Jr. et al.

[11] Patent Number: 4,549,655
[45] Date of Patent: Oct. 29, 1985

[54] CONTAINER FOR A LAYERED CHEMICAL ANALYSIS SYSTEM

[75] Inventors: Jesse G. Forsythe, Jr., Media; Sally S. Stafford, Chadds Ford, both of Pa.

[73] Assignee: E. I. Du Pont de Nemours and Company, Wilmington, Del.

[21] Appl. No.: 558,311

[22] Filed: Dec. 5, 1983

[51] Int. Cl.[4] .................. C12K 1/10; G01N 31/00
[52] U.S. Cl. .................. 206/569; 206/445; 206/456; 422/58; 422/102
[58] Field of Search ........... 206/445, 451, 456, 526, 206/569, 572; 422/50, 58, 61, 68, 99, 102, 105

[56] References Cited

U.S. PATENT DOCUMENTS

| 2,785,057 | 3/1957 | Schwab et al. | 422/58 |
|---|---|---|---|
| 3,368,872 | 2/1968 | Natelson | |
| 3,378,347 | 4/1968 | Saravis | 422/58 |
| 3,389,966 | 6/1968 | Saravis | 422/58 |
| 3,390,962 | 7/1968 | Goldsmith | 422/58 |
| 3,723,064 | 3/1973 | Liotta | 23/230 |
| 3,990,852 | 11/1976 | Piazzi | 422/102 |
| 4,178,153 | 12/1979 | Sodickson | 422/58 |
| 4,246,339 | 1/1981 | Cole et al. | 422/102 |
| 4,258,001 | 3/1981 | Pierce et al. | 422/56 |
| 4,304,865 | 12/1981 | O'Brien et al. | 422/102 |
| 4,356,149 | 10/1982 | Kitajima et al. | 422/56 |

FOREIGN PATENT DOCUMENTS

| 51183 | 10/1981 | European Pat. Off. |
| 2111676 | 10/1981 | United Kingdom |
| 2090659 | 12/1981 | United Kingdom |

*Primary Examiner*—George E. Lowrance
*Assistant Examiner*—Jimmy G. Foster

[57] ABSTRACT

A container for a layered chemical analysis system includes a first, rigid, member and a second, flexible, member. The flexible member is moveable with respect to the rigid member from a first, unstressed, position to a second, stressed, position in which the flexible member is flexed to generate a reaction force acting in a direction substantially normal to stacked layers to thereby urge the same into intimate contact with each other.

25 Claims, 8 Drawing Figures

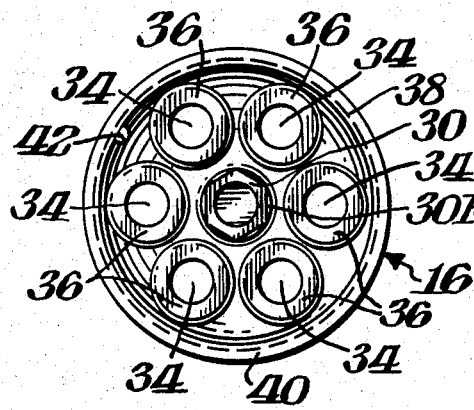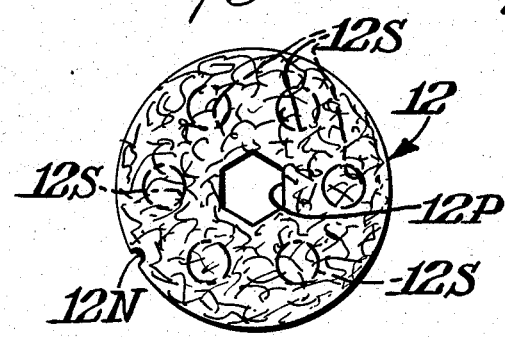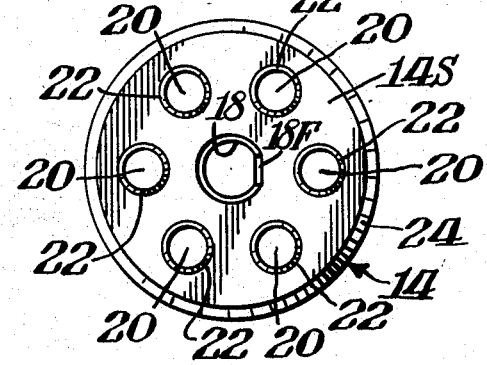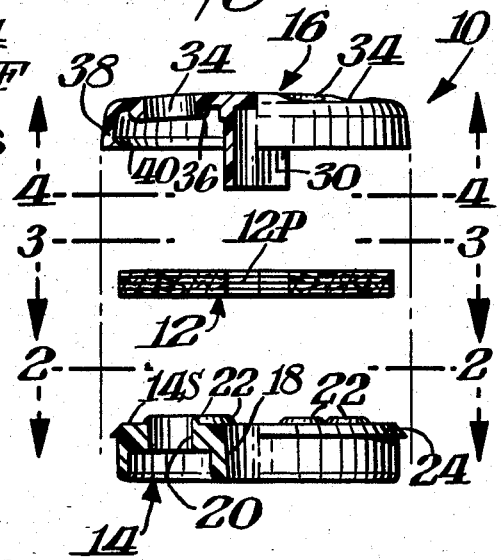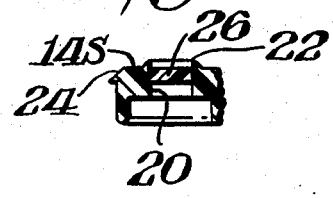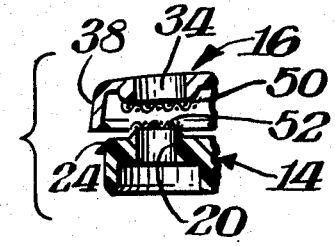

CONTAINER FOR A LAYERED CHEMICAL ANALYSIS SYSTEM

BACKGROUND OF THE INVENTION

1. Field of the Invention

This invention relates to a container for a layered chemical analysis system utilizing a plurality of layers of material which must be confined in intimate contact with each other in order to effectively perform the analysis.

2. Description of the Prior Art

Layerd chemical analysis systems of various types have been well known for some time. Typical of such analysis systems are those disclosed in U.S. Pat. Nos. 3,723,064 (Liotta); 4,356,149 (Kitajima et al.); and 4,258,001 (Pierce et al.); EPO Application No. 51,183, Published May 12, 1982 (Akiyoshi), and British Pat. No. 2,111,676 (Liotta). Such analysis systems typically include a layered stack of materials which may be impregnated with various chemical reagents necessary to carry out the desired sequence of reactions. The typical mode of use is to deposit a sample under test onto a layer of the stack and to permit that sample to pass through or into the layers. The existence of a constituent of interest in the sample is typically denoted by the presence or absence of a predetermined indication, for example, the appearance of a colored reaction product.

It has been noted that sample passage through the layers in such analysis systems can be virtually nonexistent or inconsistent unless the layers of the stack are in intimate contact with each other. To provide such contact, in some analysis systems the layered stack of materials is held together by applying adhesive circumferentially about its edge, or by adhering the layers to each other by adhesive disposed therebetween. However, the former expedient may not maintain the layers in the necessary intimate contact, while with the latter, the adhesive must be porous and not interactive with the sample, and the layers will not be readily separable. Moreover, each expedient requires added manufacturing steps.

As an alternative a stretch/shrink filament or film could be utilized to hold together the layered stack of materials. However, this is basically a variation of circumferential banding of the stack and would not appear to supply the required normal force to hold the layers in intimate contact due to the mechanics of the geometry of the stack.

In view of the foregoing, therefore, it is believed advantageous to provide a container for a layered chemical analysis system which exerts the required compressive force in a direction normal to the layered stack of materials to compress the same into intimate contact with each other. Further, it is believed advantageous to provide a container arrangement which permits access to both the upper and lower layers in the stack. Such access may be desirable, for example, respectively to permit deposition thereon of the sample under test or to view the indication produced by the sample. Yet further, it would be advantageous to provide a container which is adapted to provide a predetermined multiplicity of test sites, with each test site in a container having substantially the same magnitude of normally directed compressive force exerted on the layered stack. Still further advantage is believed provided if each of a plurality of containers can be assured to provide compressive forces of substantially equal magnitude on the layered stacks therein. Yet further, it is believed advantageous to provide a container which is easy to assemble and use and which has members which occupy a first position relative to each other to receive and hold the layers of the stack and thereafter move with respect to each other into closed contact to exert the requisite normal force on the layered stack.

SUMMARY OF THE INVENTION

The present invention relates to a container for a layered chemical analysis system of the type hereinabove set forth that includes a stacked plurality of layers of material which must be held in intimate contact with each other by a substantially normally directed compressive force in order to efficaciously perform the analysis. The container comprises a pair of mateable members, either one of which may, as circumstances require, define the upper member of the pair while the other member defines the complimentary lower member. One of the members is substantially rigid while the other is flexible. The resilient member is movable with respect to the rigid member from a first, unstressed, position to a second, stressed, position. While in the second position the flexible member is adapted to flex thus generating a reaction force which acts on the stacked layers of the chemical analysis system in a direction substantially normal thereto to thereby compress the layers into intimate contact with each other.

In the preferred embodiment, the rigid member is a substantially planar member having a plurality of openings arranged therein. The flexible member is, in the preferred case, an inverted cup-shaped member having a corresponding plurality of openings therein. An indexing arrangement is provided in the form of a post depending downwardly from the surface of one of the members cooperable with a flat surface on a registration port formed centrally and axially through the other of the members. When the post is placed into the registration port the openings in the flexible member are vertically registered with the openings in the rigid member. The rim of the flexible member is provided with a flange which is adapted to mate with a corresponding ridge provided on the periphery of the rigid member. With the flexible member in the second position the flange thereon is snappingly received over and retained by the ridge to thereby secure the flexible member in the stressed position. In the preferred embodiment of post engagement with the other of the members, the post assists in securing the flexible member in the stressed position by having a small tapered interference fit.

Both the underside of the flexible member and the rigid member may have raised annular protrusions surrounding the respective openings therein such that with the flexible member in the second position the upraised protrusions more firmly compress those portions of the layers disposed therebetween to confine a drop of sample under test introduced through a given opening within that region of the stacked layers viewable through the corresponding opening. The openings may have a mesh or membrane thereover to define a sample cup adapted to hold a sample under test away from the adjacent layer of the stack until the flexible member is moved to the second, stressed, position.

BRIEF DESCRIPTION OF THE DRAWINGS

The invention will be more fully understood from the following detailed description thereof taken in connection with the accompanying drawings which form a part of this application and in which:

FIG. 1 is an exploded view of the container in accordance with the present invention with the members thereof shown partially in section;

FIG. 2 is a plan view of the rigid member of the container in accordance with the present invention taken along view lines 2—2 in FIG. 1;

FIG. 3 is a plan view of the layered stack of chemical analysis system carried by the container of the present invention taken along view lines 3—3 in FIG. 1;

FIG. 4 is a bottom view of the flexible member of the container in accordance with the present invention taken along view lines 4—4 in FIG. 1;

FIG. 5 is an enlarged partial section showing an alternate embodiment of the rigid member of a container in accordance with the present invention;

FIG. 6 is an enlarged partial section view showing an alternate embodiment of the rigid and flexible members of the container in accordance with the present invention.

DETAILED DESCRIPTION OF THE INVENTION

Figure 7:
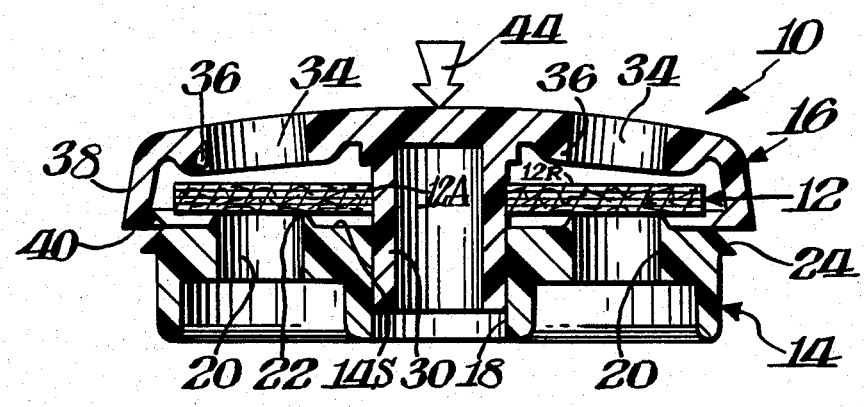
FIG. 7 and FIG. 8 are, respectively, views of the container showing the flexible member in the first, unstressed, position and in the second, stressed, position.

Throughout the following detailed description similar reference numerals refer to similar elements in all figures of the drawings.

With reference to the Figures shown is a container in accordance with the present invention generally indicated by reference character 10. The container 10 is useful to hold a layered stack 12 of materials needed to perform a predetermined layered chemical analysis. The stack 12 may hold any predetermined number of layers of material consistent with the particular analysis being performed. The stack 12 is preferably substantially circular in plan and has a central passage 12P of hexagonal cross section extending therethrough and a notch 12N therein, both for purposes which become apparent herein. Of course, the layers of the stack 12 and the passage 12P therethrough can take any convenient configuration with the container 10 therefore appropriately corresponding in shape.

The container 10 is adapted to receive and support the layered stack 12 corresponding to the chemical analysis of interest and to compress the constituent layers of material into intimate contact with each other. The container 10 comprises a first, or rigid, member 14 and a second, or flexible, member 16 which is moveable with respect to the rigid member 14 from a first, unstressed, position (FIG. 7) to a second, stressed, position (FIG. 8). When in the second position, as will be discussed herein, the flexible member 16 is flexed to generate a reaction force which acts on the layers of the stack 12 in a direction substantially normal thereto to compress the layers of the stack into intimate contact with each other. As will be developed herein, either the first member 14 or the second member 16 may be operatively used above or below the stack 12 and remain within the contemplation of the present invention. However, to facilitate discussion, it is assumed that the rigid member 14 is disposed beneath the stack 12 while the flexible member is disposed thereabove. Accordingly, hereafter the first, rigid, member 14 shall be referred to as the "base" while the second, flexible, member 16 will be referred to as the "cover". Both the base 14 and the cover 16 are molded or otherwise suitably manufactured from any suitable material, such as low density polyethylene, which is both sufficiently structurally stable to form the support surface 14S on the base 14 and sufficiently resilient to impart flexibility to the cover 16. Alternatively, the base 14 may be molded of an optically transparent, rigid material such as polystyrene.

With reference to FIGS. 1 and 2 the base 14 is a substantially cylindrical disk-like member having a support surface 14S thereon. The perimeter of the surface 14S conforms to the perimetric configuration of the stack 12. The base 14 has a tapered central and axial registration port 18 extending therethrough. One portion 18F of the boundary of the port 18 is flattened for a purpose discussed herein. An array of openings 20 is disposed through that annular portion of the surface 14S of the base member 14 which surrounds the registration port 18. A protrusion 22 surrounds each of the registration openings 20 for a purpose also discussed more fully herein. Surrounding the base 14 portion is a circumferential ridge 24. As an alternate embodiment, as shown in FIG. 5, the openings 20 may be provided with a transparent window 26 through which the results of the analysis may be viewed. The window 26 may also provide suitable isolation to limit air contact with sensitive layers of the stack. The base 14, including the window 26, is preferably fabricated or molded as a unit. The surface of the window 26 is coplanar with the surface 14S of the base 14.

As shown in FIGS. 1 and 3 the cover 16 is a flexible, substantially inverted cup-like member. The cover 16 corresponds to the shape of the base 14 and has a downwardly depending registration post 30 depending therefrom. The registration post 30 has a predetermined cross-sectional configuration that includes at least one flattened surface 30F. As shown in FIG. 3 the post 30 exhibits a hexagonal cross-section although any convenient shape may be used. The passage 12P in the stack 12 preferably, but not necessarily, corresponds to the shape of the post 30. The diameter of a circle inscribing the post 30 is slightly larger than the smallest diameter of the tapered registration port 18. Of course, the post 30 may be disposed on the base 14 while the registration port 18 may be provided in the cover 16 and remain within the contemplation of the present invention.

The cover 16 has an array of access openings 34 disposed therein. The openings 20 and 34, in the base 14 and the cover 16, respectively, may take any convenient shape. The access openings 34 extend through that annular portion of the cover 16 surrounding the registration post 30. On the undersurface of the cover 16 a protrusion 36 surrounds each of the sample access openings 34. A skirt 38 extends downwardly from the periphery of the cover 16. The inner portion of the rim of the skirt 38 is provided with a circumferential flange 40. The underside of the cover 16 is provided with a protrusion 42. The protrusion 42 is sized to register with and be received by the cutout 12N in the stack 12. This insures the registrability of the same reaction site 12S defined on the stack 12 beneath a registered pair of openings in the cover and base. The cover 16 may be provided with predetermined indicia (not shown) to assist in coordinating the location of predetermined test sites 12S with the particular pair of openings in the cover and base corresponding to the indicia. Of course, any predetermined number of test sites may be afforded by the container 10.

Figure 8:
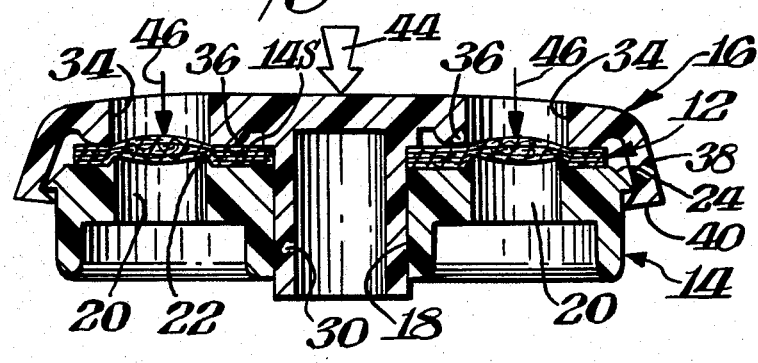

In operation and use, with reference to FIGS. 7 and 8, a stack 12 containing the necessary layers for a chemical analysis is disposed on, received and supported by the support surface 14S of the base member 14. The post 30 depending downwardly from the cover 16 extends through the passage 12P in the stack 12 and is inserted into the registration port 18 provided in the base 14. One of the flats 30F on the registration post 30 is aligned with the registration flat 18F which defines one boundary of the port 18 to thereby insure vertical registry between the viewing openings 20 provided in the base 14 and the sample access openings 34 provided in the cover 16. Owing to the discrepancy in diameters, the post 30 is snugly received within the port 18. Since the port 18 is tapered, initial entry of the post 30 into the port 18 is relatively facile, with the snugness of fit developing as the post 30 is advanced into the port 18.

The cover 16 is then moved in the closing direction indicated by the arrow 44 until the ridge 40 on the skirt 38 just touches the periphery of the ridge 24 on the base 14. This relationship of the cover and the base (shown in FIG. 7) defines the first, unstressed, position of the cover 16 with respect to the base 14. The stack 12 is contained within that annular region defined by the undersurface of the cover 16, the inner surface of the skirt portion 38 and the support surface 14S of the base 14.

Thereafter, further movement of the cover 16 with respect to the base 14 in the closing direction 44 displaces the cover 16 from the first, unstressed, position (FIG. 7) to the second, stressed, position (FIG. 8). As the cover 16 displaces to this position, the flange 40 on the cover 16 rides outwardly over the ridge 24 until the flange 40 is snappingly engaged over the ridge 24 when in the second position. While in the second position the cover 16 is flexed to generate a reaction force which acts on the stack 12 in a direction 46 substantially normal to the stack 12 to compress the layers of the same into intimate contact with each other thereby to enhance the passage of the sample through the layers of the analysis.

As may be seen in FIGS. 7 and 8, in the unstressed condition the cover is arched away from the base 14 (the degree of arch is exaggerated for purposes of clarity of illustration in FIG. 7). The basically bowed configuration of the cover 16 is imparted thereto during manufacture. However, in the stressed position shown in FIG. 8 the cover is flattened, which action generates the above-discussed reaction force which tends to compress the stack 12. In the preferred case, the engagement of the post 30 with the port 18 assists in securing the cover 16 in the stressed position. The pinching action afforded by the cooperative association of the protrusions 22 and 36 on the base 14 and cover 16, respectively, serve to "pinch-off" or more securely segregate portion of the stack 12 caught therebetween to mitigate migration of the sample to other regions of the stack 12. Migration of the sample may be further prevented by appropriately treating a predetermined portion of the layers (or only the upper layer) of the stack 12. This results in the definition of the predetermined sites 12S through which sample passage is permitted. As discussed earlier, registration of the sites 12S with respect to the openings 20 and 38 is facilitated by the cooperative association of the protrusion 42 with the notch 12N in the stack 12. With the stack 12 compressed between the cover 16 and the base 14 (as shown in FIG. 8) a sample under test may be introduced onto the stack 12 through the appropriate access openings 34 or 20, as the case may be. After a predetermined time the results of the analysis may be viewed through the other of the openings 20 or 34. If necessary, further reagents may be introduced through either of the openings 20 or 34.

In some instances, if the nature of the analysis so requires, it may be necessary or desirable to introduce the sample simultaneously onto all test sites 12S of the stack 12. To satisfy this need, a sheet 50, 52 of porous material is bridged across the protrusions 22 and 36 on one of the base 14 and cover 16, respectively, (whichever is to be the upper of the two members). This alternate embodiment of the invention is shown in FIG. 6. The sheet 50 or 52 (as the case may be) transforms the openings in the cover 16 or the base 14 into cup-like regions. A sample introduced into each cup (with the container in the unstressed position) will be held in the cup until the sample contacts the stack through the sheet as the compressive action of the container occurs. This provides equality of reaction time for all sites used. A time delay prior to the contact with the stack can also be provided in this way, if needed or desired for a step in the analysis. The sheets or cups may contain the necessary reagent; alternately reagents may be preliminarily added to the sample before the sample is introduced into the cup. After the necessary or desired delay, the container may be closed. Suitable for use as the sheets are, for example, nylon mesh, filtration membrane, or any other material of suitable porosity which can be bonded to the edges of the protrusions.

In view of the foregoing those skilled in the art may readily appreciate that a container in accordance with this invention imparts a repeatable, reproducible compressive normal force onto the stacked layers of a layered chemical analysis system which permits and enables sample passage therethrough. The members of the container are interchangeably usable both above or below the layered stack. Each member affords ease of access to deposit sample, view analysis results, add further reagent, or other necessary operations for the analysis. Each test site within a stack housed in a particular container is exposed to substantially equal compressive force. Moreover, substantially equal compressive forces are exerted by each container on the stack therein, eliminating to a large extent uncertainty in this regard. Each container may be configured to provide any predetermined number of test sites therein. The container is easy to use and assists in confining sample passage to only the predetermined desired sites in the stack. Since time delay in sample introduction may be afforded as discussed above, the container 10 in accordance herewith is particularly useful for multilayered immunoassays.

Those skilled in the art, having the benefit of the teachings of the present invention as is hereinabove set forth may effect numerous modifications thereto. These modifications are to be construed as lying within the scope of the present invention as defined by the appended claims.

What is claimed is:

1. A container for a layered chemical analysis system of the type having a stack containing a plurality of layers of material, the stack having a plurality of test sites defined thereon, the container comprising:

a first, rigid, member;

a second, flexible, normally bowed member moveable with respect to the rigid member from a first, unstressed, position to a second, stressed, position; and means for engaging the first and second members to define a space therebetween to contain the stack while in the second position the flexible member being flexed and flattened with respect to the rigid member to generate a reaction force which acts with substantially equal magnitude on the layers of the stack at each test site in a direction substantially normal thereto to compress uniformly the same between the members into imtimate contact with each other.

2. The container of claim 1 wherein the flexible member has an opening therein and wherein the rigid member has an opening therein registrable with the opening in the flexible member.

3. The container of claim 2 further comprising an index arrangement for disposing the openings in the members in registration with each other.

4. The container of claim 3 wherein the index arrangement comprises a post depending from one of the members, the post having a registration surface thereon, and a registration port in the other of the members having a corresponding registration surface thereon.

5. The container of claim 4 wherein the stack has a reaction site thereon and a notch therein, and wherein one of the members has a protrusion thereon, the protrusion being adapted to engage the notch to thereby position the reaction site between the registrable openings in the members.

6. The container of claim 2 wherein one of the members has a circumference flange and the other member has a circumferential ridge, the flange being snappingly engageable with the ridge as the flexible member moves from the first to the second position to thereby secure the members to each other.

7. The container of claim 6 further comprising an index arrangement for disposing the openings in the members in registration with each other.

8. The container of claim 7 wherein the index arrangement comprises a post depending from one of the members, the post having a registration surface thereon, and a registration post in the other of the members having a corresponding registration surface thereon.

9. The container of claim 8 wherein the stack has a reaction site thereon and a notch therein, and wherein one of the members has a protrusion thereon, the protrusion being adapted to engage the notch to thereby position the reaction site between the registrable openings in the members.

10. The container of claim 3 wherein the flexible member and the rigid member each have a protrusion surrounding the opening therein, the protrusions being cooperable to segregate a portion of the layers pinched therebetwen.

11. The container of claim 6 wherein the flexible member and the rigid member each have a protrusion surrounding the openings therein, the protrusions being cooperable to segregate a portion of the layers pinched therebetween.

12. The container of claim 10 wherein a porous layer is disposed across the protrusion on one of the members to cooperate with the opening therein to define a sample-receiving cup.

13. The container of claim 11 wherein a porous layer is disposed across the protrusion on one of the members to cooperate with the opening therein to define a sample-receiving cup.

14. The container of claim 3 wherein the opening in one of the members has a transparent window therein.

15. The container of claim 10 wherein the opening in one of the members has a transparent window therein.

16. The container of claim 6 wherein the opening in one of the members has a transparent window therein.

17. The container of claim 11 wherein the opening in one of the members has a transparent window therein.

18. A container for a layered chemical analysis system of the type having a stack containing a plurality of layers of material, the stack having a plurality of test sites defined thereon, the container comprising:

a first, rigid, member; and a second, flexible, normally bowed member;

one of the members being adapted to receive and support the layers of the stack;

the second, flexible, member being moveable with respect to the first member from a first, unstressed, position to a second, stressed, position;

while in the stressed position the flexible member being flexed and flattened with respect to the rigid member to generate a reaction force which acts on the layers of the stack at each test site in a direction substantially normal thereto to compress uniformly the same between the members into intimate contact with each other;

each of the members having an opening therein registrable with the opening in the other, one of the openings defining an access opening through which a sample under test may be introduced onto the layers of the stack;

one member having a circumferential flange and the other member has a circumferential ridge thereon, the flange being snappingly engageable with the ridge as the flexible member moves from the first to the second position to thereby secure the members.

19. The container of claim 18 further comprising an index arrangement for registering the openings in registration with each other, the index arrangement comprising a post depending from one of the members, the post having a registration surface thereon, and a tapered registration port in the other of the members, the port having a corresponding registration surface thereon, such that insertion of the post into the port snugly securing the members to each other with the openings therein in registration.

20. The container of claim 18 wherein the flexible member and the rigid member each have a protrusion surrounding the openings therein, the protrusion being cooperable to segregate a portion of the layers pinched therebetween to define a reaction site in the layered stack.

21. The container of claim 18 wherein the opening in one of the members has a transparent window therein.

22. The container of claim 19 wherein the opening in one of the members has a transparent window therein.

23. The container of claim 20 wherein the opening in one of the members has a transparent window therein.

24. The container of claim 23 wherein a porous layer is disposed across the protrusion on the other of the members to cooperate with the opening therein to define a sample-receiving cup.

25. The container of claim 20 wherein a porous layer is disposed across the protrusion on one of the members to cooperate with the opening therein to define a sample-receiving cup.

* * * * *